United States Patent
Frings

(10) Patent No.: US 9,757,139 B2
(45) Date of Patent: Sep. 12, 2017

(54) MEDICAL GRIPPING TOOL

(71) Applicant: Karl Storz GmbH & Co. KG, Tuttlingen (DE)

(72) Inventor: Hermann-Josef Frings, Aachen (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 565 days.

(21) Appl. No.: 14/340,962

(22) Filed: Jul. 25, 2014

(65) Prior Publication Data

US 2015/0032152 A1 Jan. 29, 2015

(30) Foreign Application Priority Data

Jul. 25, 2013 (DE) ........................ 10 2013 107 972

(51) Int. Cl.
| | | |
|---|---|---|
| *A61B 17/00* | (2006.01) | |
| *A61B 17/29* | (2006.01) | |
| *B25J 15/12* | (2006.01) | |
| *A61B 17/28* | (2006.01) | |

(52) U.S. Cl.
CPC ............ *A61B 17/29* (2013.01); *A61B 17/282* (2013.01); *B25J 15/12* (2013.01); *A61B 2017/00862* (2013.01); *A61B 2017/2926* (2013.01); *A61B 2017/2937* (2013.01); *A61B 2017/2945* (2013.01)

(58) Field of Classification Search
CPC .......... A61B 17/29; A61B 2017/00862; A61B 2017/2926; A61B 17/282; A61B 2017/2937; A61B 2017/2945; A61B 10/06; A61B 17/22031; A61B 17/221; B25J 15/12; B25J 15/0009; B25J 15/10; B25J 15/106; B25B 7/02; B25B 9/00; Y10S 294/902
USPC ......... 606/151–158, 207; 294/104, 106, 197, 294/902; 414/739; 81/487; 901/39
See application file for complete search history.

(56) References Cited

U.S. PATENT DOCUMENTS

| | | | |
|---|---|---|---|
| 4,367,891 A | | 1/1983 | Wauer et al. |
| 5,250,072 A | * | 10/1993 | Jain ...................... A61B 17/282 606/205 |
| 2010/0263500 A1 | | 10/2010 | Bannasch et al. |

(Continued)

FOREIGN PATENT DOCUMENTS

| | | |
|---|---|---|
| DE | 10031773 A1 | 11/2001 |
| DE | 102007026721 A1 | 5/2008 |
| DE | 102007050018 A1 | 5/2008 |

(Continued)

OTHER PUBLICATIONS

English machine translation of DE 102007026721 A1, published May 15, 2008 to Hoelscher et al.*

*Primary Examiner* — Katherine M Shi

(74) *Attorney, Agent, or Firm* — Whitmyer IP Group LLC

(57) ABSTRACT

In a medical gripping tool with several branches, one branch includes a first flexurally elastic spar, a second flexurally elastic spar, of which the distal end is connected to the distal end of the first flexurally elastic spar, a rib, which is spaced apart from the proximal ends and from the distal ends of the flexurally elastic spars, and a linear guide for coupling the second flexurally elastic spar to the rib, in such a way that a linear movement of the second flexurally elastic spar relative to the rib is possible.

14 Claims, 2 Drawing Sheets

(56) References Cited

U.S. PATENT DOCUMENTS

2011/0034918 A1* 2/2011 Reschke ............ A61B 17/2812
606/41

FOREIGN PATENT DOCUMENTS

| DE | 102010009259 A1 | 8/2011 |
| DE | 102010022431 A1 | 12/2011 |
| EP | 2502714 A1 | 9/2012 |

* cited by examiner

MEDICAL GRIPPING TOOL

FIELD OF THE INVENTION

The present invention relates to a medical gripping tool, in particular for microinvasive interventions.

BACKGROUND OF THE INVENTION

In medical interventions, it is often the case that vessels, organs, tissues or other medical objects cannot be gripped and held directly by hand. This applies in particular in microinvasive interventions. In these cases, gripping tools are used. These constitute forceps, at least in the broader sense. For different uses, in particular for tissue with different mechanical properties and of different sensitivity, a wide range of different medical gripping tools are available in order to permit gripping and holding in a way that is safe and at the same time gentle and non-traumatic.

DE 10 2007 026 721 A1 and DE 10 2010 009 259 A1 describe shape-adaptive medical gripping tools based on the fin ray effect. DE 10 2007 050 018 A1 describes a medical gripping tool with spring elements in fluid chambers or for supporting gripping surfaces.

A medical gripping tool based on the fin ray effect can adapt at least partially to the shape of a gripped or held object. The size of the contact surface between gripping tool and gripped object can thus be increased. Moreover, it permits gripping that is based partially on a form fit. However, further improvements are desirable in order in particular to permit still more sensitive gripping.

SUMMARY OF THE INVENTION

It is an object of the present invention to make available an improved medical gripping tool and an improved medical instrument.

This object is achieved by the subject matter of the independent claims.

Developments are set forth in the dependent claims.

Embodiments of the present invention are based on the concept whereby transverse connections between the flexurally elastic spars of a branch are created not via hinges but instead via linear guides.

In a medical gripping tool with several branches, each branch comprises a first flexurally elastic spar, a second flexurally elastic spar, of which the distal end is connected to the distal end of the first flexurally elastic spar, a rib, which is spaced apart from the proximal ends and from the distal ends of the flexurally elastic spars, and a linear guide for coupling the second flexurally elastic spar to the rib, in such a way that a linear movement of the second flexurally elastic spar relative to the rib is possible.

The medical gripping tool can have two or more branches, in particular three or four branches. All the branches of the medical gripping tool can be of identical or similar configuration. Alternatively, for example, one or more branches are rigid, and one or more further branches have the described features and, in particular, in each case at least one linear guide.

The distal ends of the two flexurally elastic spars are in particular connected to each other directly and rigidly. In particular, the distal ends of the flexurally elastic spars are connected to each other by cohesive bonding (for example by welding, soldering or adhesion) and/or with a form fit or are formed by a common casting. Alternatively, the distal ends of the flexurally elastic spars can be connected to each other by a hinge, in particular a flexure bearing.

The linear guide permits in particular a movement of the second flexurally elastic spar relative to the rib in a direction parallel to the second flexurally elastic spar. In other words, the second flexurally elastic spar is movable in its longitudinal direction relative to the rib, by means of the linear guide, and is guided perpendicularly thereto with minimal play and friction.

A linear guide is a very substantially miniaturizable alternative to a hinge. In contrast to a likewise very substantially miniaturizable flexure bearing, a linear guide does not generate any elastic forces. The linear guide can therefore permit even more sensitive gripping by the medical gripping tool than is possible with a conventional flexure bearing between rib and spar.

The second flexurally elastic spar and the rib can have the same or different materials. In particular, the rib can be made from plastic (for example cast in one piece with the first flexurally elastic spar), and the second flexurally elastic spar can be made from a metal wire. Since no miniaturized flexure bearings are needed, it is also alternatively possible for the first flexurally elastic spar and the rib to be made in each case from metal. Compared to a conventional medical gripping tool which is based on the fin ray effect and has flexure bearings and is therefore generally made from plastic, it is possible for other materials to be used in a medical gripping tool with a linear guide. This can permit a much more extensive adaptation of all the mechanical properties of the branches of the medical gripping tool to the requirements that arise from the intended use.

In particular, in the medical gripping tool, the first flexurally elastic spar is arranged on one side of the branch, which side faces toward an object to be gripped and toward the one or more further branches. In this case, the second flexurally elastic spar is arranged on the opposite side of the branch, i.e. the side facing away from an object to be gripped and from the one or more further branches. Alternatively, the second flexurally elastic spar is arranged on a side of the branch facing toward an object to be gripped and toward the one or more further branches.

In a medical gripping tool as described here, the rib and the first flexurally elastic spar are in particular connected rigidly to each other.

The rib and the first flexurally elastic spar are in particular connected to each other without a flexure bearing or another hinge. The rib and the first flexurally elastic spar can be produced simultaneously and in one piece, for example by means of a casting technique. Alternatively, the rib and the first flexurally elastic spar can be produced separately (from the same or different materials) and then joined by welding, adhesive bonding or joined in another way with a cohesive bond, a form fit and/or force fit. Alternatively, for example, the first flexurally elastic spar is produced first (from metal or another material) and then placed in a die in which, finally, the rib is formed integrally onto the first flexurally elastic spar.

In a medical gripping tool as described here, the linear guide in particular comprises a recess in the rib, in which recess the second flexurally elastic spar is guided displaceably in its longitudinal direction.

The recess is in particular a channel or a continuous bore with a cross section which corresponds to the cross section of the second flexurally elastic spar at the location of the rib, in such a way that the second flexurally elastic spar is guided in the channel or bore with minimal play and friction. Alternatively, for example, the second flexurally elastic spar has the shape of a T-beam or I-beam or H-beam, and the recess has the shape of an (inverted) T.

In a medical gripping tool as described here, the linear guide in particular comprises an eyelet in which the second flexurally elastic spar is guided displaceably in its longitudinal direction.

A recess in the rib can be designed as an eyelet. Alternatively, the eyelet can be designed as an annular device. In this case, the eyelet can be formed integrally with the rib and in particular can be produced in one piece together with the rib or can be designed as a component part that is produced separately and that is then joined to the rib.

In a medical gripping tool as described here, several ribs in particular are provided which are spaced apart from the proximal ends and from the distal ends of the flexurally elastic spars and from each other, wherein on each of the several ribs a linear guide is provided which permits a movement of the second flexurally elastic spar relative to the rib.

In a medical gripping tool with several ribs, such as is described here, the distance on the rib between the linear guide and the first flexurally elastic spar is all the smaller, the smaller the distance of the rib from the distal ends of the spars.

A medical gripping tool as described here in particular also comprises a fluting on the first flexurally elastic spar.

Alternatively or in addition, a medical gripping tool as described here can comprise a fluting on the second flexurally elastic spar.

A fluting on one of the two flexurally elastic spars can increase the flexural elasticity of the latter. In particular, a fluting on the flexurally elastic spar facing toward an object to be gripped, and toward the one or more further branches, can improve the force fit between the branch and the associated object and/or can supplement a form fit.

In a medical gripping tool as described here, the first flexurally elastic spar in particular comprises at least either two flexurally elastic rods or a strip-shaped/plate-shaped component.

The two or more flexurally elastic rods are in particular arranged parallel or substantially parallel (for example with spaces between them decreasing in the distal direction). The flexurally elastic rods and also the strip-shaped/plate-shaped component can be made from metal or another elastic material. The flexurally elastic rods and/or the strip-shaped/plate-shaped component are in particular joined to the rib or ribs by cohesive bonding, a form fit and/or a force fit. In particular, the flexurally elastic rods or the strip-shaped/plate-shaped component are arranged in a corresponding recess in the rib and are held with a force fit (optionally also with cohesive bonding and/or a form fit).

A medical gripping tool as described here also in particular comprises a fluting on the first flexurally elastic spar.

In particular, the first flexurally elastic spar is undulated in the longitudinal direction. For example, the first flexurally elastic spar is produced from an undulated strip of sheet metal. If the flexurally elastic spars in the branch are arranged such that the second flexurally elastic spar is arranged on a side of the branch facing toward an object to be gripped or toward one or more branches, then, instead of the first flexurally elastic spar, the second flexurally elastic spar is designed at least partially with a fluting or is undulated in the longitudinal direction.

A medical gripping tool as described here also in particular comprises a spacer sleeve on the first flexurally elastic spar, which spacer sleeve defines a distance of the rib from the proximal end or a distance of the rib from the distal end of the first flexurally elastic spar or a distance of the rib from a further rib.

The spacer sleeve has in particular the shape of a tube with a cross section corresponding to the first flexurally elastic spar. If the first flexurally elastic spar has one or more (in particular parallel or substantially parallel) rods, spacer sleeves can be provided on one or more of the rods. The spacer sleeves are designed, for example, as flexible tubes made of PTFE or another elastic material.

In the simplest approach during assembly, spacer sleeves and ribs are engaged alternately onto the first flexurally elastic spar. In this way, the number of necessary welded, adhesively bonded or other connections can be considerably reduced.

In a medical gripping tool as described here, the first flexurally elastic spar, the second flexurally elastic spar and the rib are in particular at least partially encapsulated by an elastic material.

In particular, the flexurally elastic spars and the rib or ribs are partially or completely encapsulated with silicone, rubber, an elastomer or another elastic material. In particular, the flexurally elastic spars and the rib or ribs are cast into the elastic material.

The encapsulation, with a smooth and closed surface, can improve the cleaning and sterilization of the medical gripping tool. The elastic material can also contribute to protecting objects that are gripped by means of the medical gripping tool and can improve the force fit between the medical gripping tool and a gripped object.

A medical gripping tool as described here also in particular comprises a hinge between the proximal end of a branch and a main body of the medical gripping tool.

The hinge can provide a form-fit mechanical connection, with minimal play and friction, between the branch and the main body. Alternatively, the hinge can be designed as a flexure bearing. The hinge in particular creates an articulated connection between the proximal end of one of the two flexurally elastic spars of the branch and the main body. In the case of several branches, a hinge can be provided between each of the branches and the main body.

Alternatively or in addition to a hinge between a branch and a main body, it is possible to provide a hinge via which the branch is coupled to a distal end of a push or pull rod or another transmission mechanism, in such a way that a movement of the transmission mechanism causes an opening or closing of the medical gripping tool, in particular a pivoting of the branch.

Alternatively, the gripping tool can be designed in such a way that, for opening and closing, the two branches can be moved away from each other and toward each other in parallel or substantially in parallel.

A medical gripping tool as described here also in particular comprises a mechanism for moving the proximal end of the first flexurally elastic spar or the proximal end of the second flexurally elastic spar.

The mechanism for moving the proximal end of one of the flexurally elastic spars can be a pull or push rod or another transmission mechanism or a coupling mechanism for releasable or non-releasable coupling to a transmission mechanism. The mechanism is in particular designed for moving the proximal end of one of the flexurally elastic spars parallel to a longitudinal axis of the medical gripping tool or of a shank to which the medical gripping tool is or can be connected, and/or parallel to the flexurally elastic spar itself. The mechanism is in particular designed as a pull rod and is coupled to the proximal end of the first flexurally elastic spar or is designed as a push rod and is coupled to the proximal end of the second flexurally elastic spar.

A medical instrument comprises a medical gripping tool as described here.

BRIEF DESCRIPTION OF THE DRAWINGS

Embodiments are explained in more detail below with reference to the attached figures, in which.

DETAILED DESCRIPTION OF THE INVENTION

Figure 1:
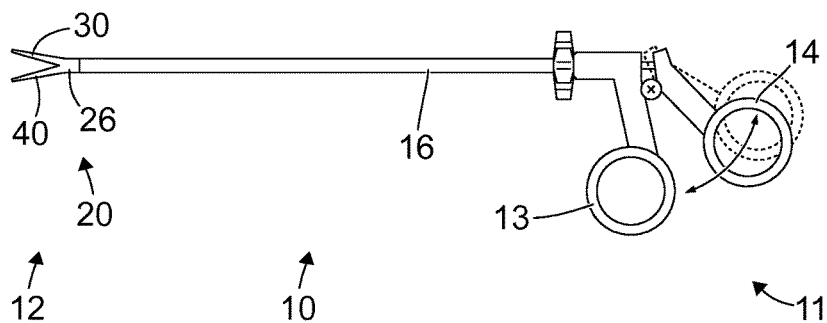
FIG. 1 shows a schematic view of a medical instrument.

FIG. 1 shows a schematic view of a medical instrument 10 with a proximal end 11 and a distal end 12. The medical instrument 10 is designed in particular for use in a microinvasive medical intervention. At the proximal end 11, the medical instrument has a stationary grip part 13 and a movable grip part 14, in particular pivotable about a pivot axis arranged orthogonally with respect to the plane of the drawing in FIG. 1. A long and thin shank 16 extends between the proximal end 11 and the distal end 12. The shank 16 can be straight (as shown in FIG. 1) or curved, rigid or flexible. At the distal end 12, the medical instrument has a medical gripping tool 20 with a main body 26 and two or more branches 30, 40.

The shank 16 accommodates a pull or push rod or another transmission mechanism by which a movement and a force generated manually on the movable grip part 14 are transmitted to the distal end 12 of the medical instrument 10. At least one of the branches 30, 40 is coupled to the transmission mechanism and is movable relative to the main body 26, in particular pivotable about a pivot axis perpendicular to the longitudinal axis of the shank 16 and of the main body 26. The main body 26 is mechanically connected to the distal end of the shank 16 in a releasable manner via a coupling. Alternatively, the main body 26 is mechanically connected to the distal end of the shank 16 permanently and in such a way that it cannot be released without being destroyed.

The medical instrument 10 can have further features and properties deviating from the view in FIG. 1 or not shown in FIG. 1. For example, the shank 16 can be rotatable, together with the medical gripping tool 20, about the longitudinal axis of the shank 16. Moreover, the medical instrument 10 can be able to be dismantled into several parts in order to make cleaning and sterilization easier.

Figure 2:
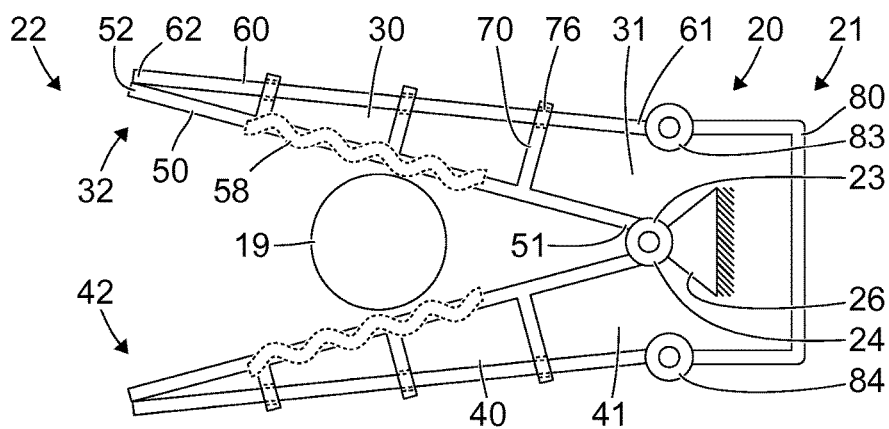
FIG. 2 shows a schematic view of a medical gripping tool.

FIG. 2 shows a schematic view of a medical gripping tool 20 which, for example, can be a constituent part of the medical instrument 10 shown in FIG. 1 or can be designed therefor.

The proximal ends 31, 41 of the branches 30, 40 of the medical gripping tool 20 are connected in an articulated manner, via hinges 23, 24, to the main body 26 of the medical gripping tool 20, which main body 26 is merely symbolized in FIG. 2. The hinges 23, 24 define pivot axes orthogonal to the plane of the drawing in FIG. 2. As is indicated in FIG. 2, both hinges 23, 24 can be combined with each other or nested one inside the other, such that the pivot axes of both branches 30, 40 are identical. Alternatively, and in contrast to the view in FIG. 2, the two hinges 23, 24 can be arranged next to each other or spaced apart from each other and can define two spaced-apart and in particular parallel pivot axes.

At the proximal end 21 of the medical gripping tool 20, a coupling mechanism 80 is also indicated, which is connected in an articulated manner to the branches 30, 40 by means of two hinges 83, 84. The coupling mechanism 80 is displaceable parallel to the longitudinal axis of a shank 16 (cf. FIG. 1), which is or can be connected to the medical gripping tool 20. The coupling mechanism 80 is connected to a push rod in the shank 16 (cf. FIG. 1) by means of a coupling (not shown) or directly and inseparably. As a result of the distance of the hinges 83, 84 between the coupling mechanism and the branches 30, 40, on the one hand, and the hinges 23, 24 between the main body 26 and the branches 30, 40, on the other hand, a movement of the coupling mechanism 80 parallel to the longitudinal axis of the shank 16 (cf. FIG. 1) causes a pivoting of the branches 30, 40 about the pivot axes defined by the hinges 23, 24.

The branches 30, 40 are designed corresponding to each other and symmetrical to each other or substantially symmetrical to each other. For this reason, only features and properties of the first branch 30 are described below.

As has already been described, the proximal end 31 of the first branch 30 is connected via the hinge 23 to the main body 26 and via the hinge 83 to the coupling mechanism 80. The distal end 32 of the first branch 30 and the distal end 42 of the second branch 40 form the distal end 22 of the medical gripping tool 20.

The first branch 30 comprises a first flexurally elastic spar 50 and a second flexurally elastic spar 60. The proximal end 51 of the first flexurally elastic spar 50 is connected via the hinge 23 to the main body 26 of the medical gripping tool 20. The proximal end 61 of the second flexurally elastic spar 60 is connected via the hinge 83 to the coupling mechanism 80.

The distal ends 52, 62 of the flexurally elastic spars 50, 60 form the distal end 32 of the first branch 30 of the medical gripping tool 20. The distal ends 52, 62 of the flexurally elastic spars 50, 60 are connected to each other rigidly or in an articulated manner, in particular by welding or adhesive bonding, or by means of a connecting component not shown in FIG. 2.

Several ribs 70 are each connected rigidly, or substantially rigidly, to the first flexurally elastic spar 50. Near an end or edge spaced apart from the first flexurally elastic spar 50, each rib 70 has a recess or continuous bore 76. The second flexurally elastic spar 60 extends through the recesses 76 of all the ribs 70. The cross sections of the lumens of the recesses 76 and the cross sections of the second flexurally elastic spar 60, in the areas where the second flexurally elastic spar 60 is arranged in the respective recess 76, correspond so substantially to each other that the second flexurally elastic spar 60 is guided in the recesses 76 of the ribs 70 with minimal play and friction.

As is described below with reference to FIG. 3, the second flexurally elastic spar 60 is movable in its longitudinal direction in the recesses 76, wherein a movement of the second flexurally elastic spar 60 in the recesses 76 entails an elastic deformation of the flexurally elastic spars 50, 60 and therefore of the entire first branch 30.

The medical gripping tool 20 is shown in an open configuration in FIG. 2. An object 19 that can be gripped by means of the medical gripping tool 20 is indicated between the branches 30, 40. The branches 30, 40 are undeformed, the flexurally elastic spars 50, 60 straight. To make the object 19 easier to grip and to reduce the risk of its slipping, it is possible, in contrast to what is shown by solid lines in FIG. 2, for the first flexurally elastic spar 50 to have a fluting 58, as is indicated by broken lines in FIG. 2. The fluting 58 is obtained in particular from a wave shape or undulation of the first flexurally elastic spar 50 in the longitudinal direction.

Figure 3:
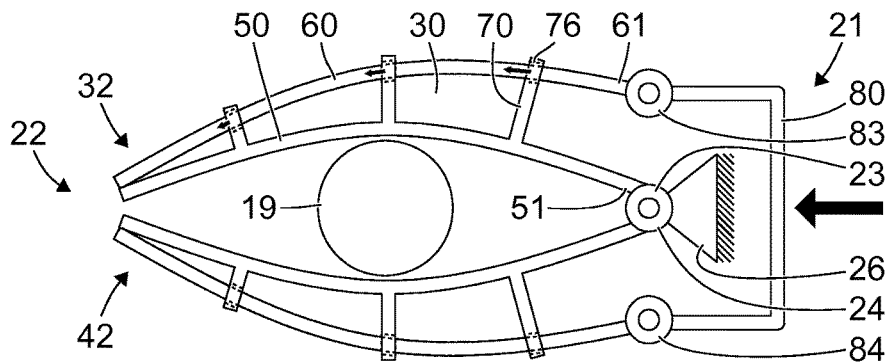
FIG. 3 shows a further schematic view of the medical gripping tool from FIG. 2.

FIG. 3 shows a further schematic view of the medical gripping tool 20 from FIG. 2. In contrast to what is shown in FIG. 2, the medical gripping tool 20 in FIG. 3 is shown in a closed configuration gripping the object 19. A large horizontal arrow indicates a force by which the coupling mechanism 80 and, with it, the hinges 83, 84 are moved relative to the main body 26 and to the hinges 23, 24 in the distal direction (to the left in the figures). The branches 30, 40 are thus pivoted so close to the object 19 that the first flexurally elastic spars 50 touch the object 19. As a result of the force pushing distally on the coupling mechanism 80, on the one hand, and as a result of the force acting between the object 19 and the first flexurally elastic spar 50, on the other hand, the flexurally elastic spars 50, 60 are elastically deformed and the second flexurally elastic spar 60 in the recesses 76 in the ribs 70 is displaced in the distal direction relative to these. The displacement of the second flexurally elastic spar 60 of the first branch 30 relative to the recesses 76 of the ribs 70 is indicated in FIG. 3 by three small arrows. As a result, the branches 30, 40 of the medical gripping tool 20 at least partially enclose the object 19. The object 19 is held by the branches 30, 40 not only with a frictional or force fit, but also with a form fit.

Figure 4:
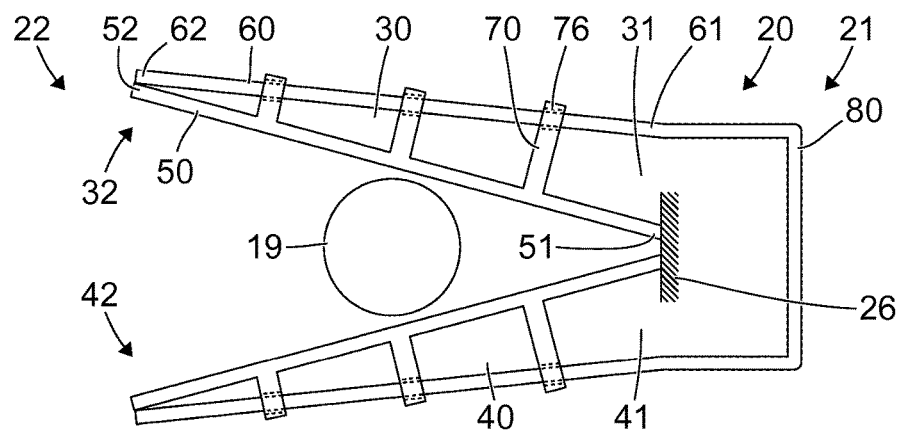
FIG. 4 shows a schematic view of a further medical gripping tool.

FIG. 4 shows a schematic view of a further medical gripping tool 20 which, in respect of some features and properties, is similar to the medical gripping tool described above with reference to FIGS. 2 and 3. Features and properties are described below by which the medical gripping tool 20 shown in FIG. 4 differs from the medical gripping tool described above with reference to FIGS. 2 and 3.

The medical gripping tool shown in FIG. 4 differs from the medical gripping tool described with reference to FIGS. 2 and 3 particularly in that no hinges are provided between the main body 26, on the one hand, and the branches 30, 40 or the first flexurally elastic spars 50, on the other hand. Instead, opening and closing of the branches 30, 40 is effected by elastic deformation of the flexurally elastic spars 50 of the branches 30, 40 near the main body 26.

The medical gripping tool 20 shown in FIG. 4 also differs from the medical gripping tool described above with reference to FIGS. 2 and 3 in that no hinges are provided between the coupling mechanism 80, on the one hand, and the branches 30, 40 or the second flexurally elastic spars 60 of the branches 30, 40, on the other hand. Instead, during opening and closing of the branches 30, 40, the second flexurally elastic spars 60 of the branches 30, 40 are elastically deformed near their proximal ends 61. Alternatively or in addition, the coupling mechanism 80 can be elastically deformed.

Figure 5:
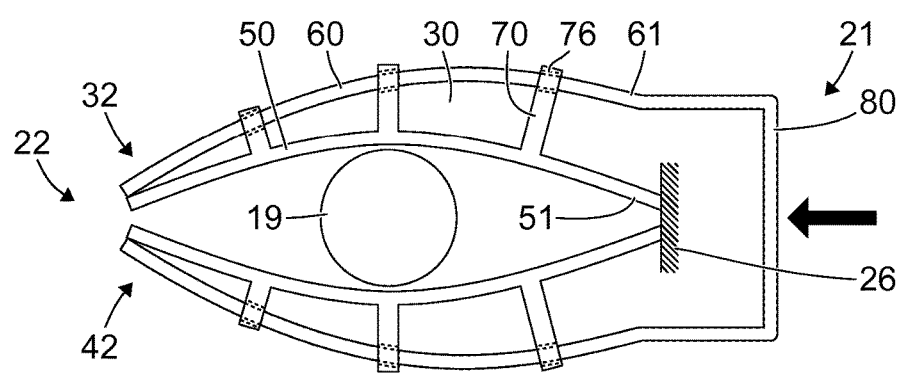
FIG. 5 shows a further schematic view of the medical gripping tool from FIG. 4.

FIG. 5 shows a further schematic view of the medical gripping tool from FIG. 4. FIG. 5, like FIG. 3, shows the medical gripping tool 20 in a closed or gripping configuration. The coupling mechanism 80 is displaced in the distal direction by a force which is indicated by a large horizontal arrow. The flexurally elastic spars 50, 60 of the branches 30, 40 are elastically deformed, the second flexurally elastic spars 60 of the branches 30, 40 are displaced in the distal direction relative to the recesses 76 in the ribs 70. The medical gripping tool 20 grips and holds the object 19 partially with a form fit.

In contrast to what is shown in FIGS. 2 to 5, the proximal ends 51 of the first flexurally elastic spars 50, for example, can be connected via hinges 23, 24 to a main body 26, and the proximal ends 61 of the second flexurally elastic spars 60 can be connected to the coupling mechanism 80 without a hinge or via a flexure bearing.

In contrast to what is shown in FIGS. 2 to 5, the proximal ends 51 of the first flexurally elastic spars 50 can be connected to a main body 26 without a hinge, and the proximal ends 61 of the second flexurally elastic spars 60 can be connected via hinges to a coupling mechanism 80.

In contrast to what is shown in FIGS. 2 to 5, the proximal ends 61 of the second flexurally elastic spars 60 can be connected (directly or via hinges) to the main body 26, and the proximal ends 51 of the first flexurally elastic spars 50 can be connected (directly or via hinges) to a transmission mechanism 80. In this case, a transmission mechanism has to transmit a tensile force for closing the branches 30, 40.

In contrast to what is shown in FIGS. 2 to 5, one branch can be rigid, and the other branch can be movable by means of the transmission mechanism 80. In contrast to what is shown in FIGS. 2 to 5, more than two branches can be provided, of which in particular at most one is rigid, and of which in particular at least one is pivotable.

Figure 6:
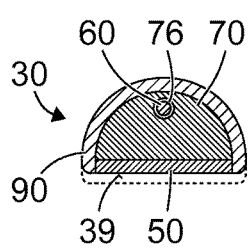
FIG. 6 shows a schematic view of a section through a branch of a medical gripping tool.

FIG. 6 shows a schematic view of a section through a branch 30 of a medical gripping tool 20 as has been described above with reference to FIGS. 2 to 5. The sectional plane in FIG. 6 is orthogonal to the planes of the drawings in FIGS. 1 to 5 and orthogonal or substantially orthogonal to the first flexurally elastic spar 50 and to the second flexurally elastic spar 60. The sectional plane in FIG. 6 intersects a rib 70 of the branch 30.

It can be seen from FIG. 6 that the first flexurally elastic spar 50 has a flat rectangular cross section. The width of the first flexurally elastic spar 50 corresponds almost to the total width of the branch 30 in the sectional plane shown in FIG. 6. The height of the cross section of the first flexurally elastic spar 5, measured orthogonally to the width and therefore in the vertical direction in FIG. 6, is substantially smaller than its width.

The rib 70 has in particular the form of a semicircular plate, which extends substantially perpendicularly with respect to the first flexurally elastic spar 50 and parallel to the plane of the drawing in FIG. 6. The rib 70 is cohesively joined to the first flexurally elastic spar 50, in particular by welding, soldering or adhesive bonding. Alternatively or in addition, the rib 70 can be joined to the first flexurally elastic spar 50 with a form fit and/or force fit or can be produced (for example cast) integrally and simultaneously therewith.

The second flexurally elastic spar 60 has the form of a thin rod and in particular has a circular cross section. The cross section of the lumen of the recess 76 is similar to the cross section of the second flexurally elastic spar 60, both in particular being circular. The cross section of the lumen of the recess 76 is slightly larger than the cross section of the second flexurally elastic spar 60, such that the second flexurally elastic spar 60 is guided in the recess 76 with minimal play and friction. In this way, the second flexurally elastic spar 60 can be moved in its longitudinal direction relative to the rib 70 (orthogonally or substantially orthogonally with respect to the sectional plane in FIG. 6).

The branch 30 has an encapsulating jacket 90, which completely encloses the branch 30 except for a gripping surface 39 on the first flexurally elastic spar 50. Alternatively, as is indicated by a broken line in FIG. 6, the jacket 90 can completely enclose the branch 30 and also form the gripping surface of the branch 30. The jacket 90 has an elastic material, for example silicone, rubber or an elastomer. Particularly if it also forms the grip surface 39, the jacket can improve the atraumatic properties of the medical gripping tool and can improve the static friction between the branch 30 and an object 19 to be gripped (cf. FIGS. 2 to 4). Moreover, the jacket 90, with a closed and smooth surface, can make the medical gripping tool easier to clean and sterilize.

Figure 7:
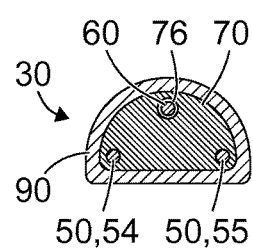
FIG. 7 shows a schematic view of a section through a branch of a further medical gripping tool.

FIG. 7 shows a schematic view of a section through a branch 30 of a further gripping tool which, in respect of some features and properties, is similar to the medical gripping tools described above with reference to FIGS. 1 to 6. The sectional plane in FIG. 7 is orthogonal to the sectional planes in FIGS. 1 to 5, orthogonal or substantially orthogonal to the flexurally elastic spars 50, 60, and corresponds to the sectional plane in FIG. 6.

In the branch 30 shown in FIG. 7, the first flexurally elastic spar 50 is formed by two parallel or substantially parallel flexurally elastic rods 54, 55. The flexurally elastic rods 54, 55 are, like the second flexurally elastic spar 60, arranged in recesses of corresponding cross sections in the rib 70. However, the cross sections of the recesses in the rib 70, in which the flexurally elastic rods 54, 55 are arranged, correspond to the cross sections of the flexurally elastic rods 54, 55, in such a way that the flexurally elastic rods 54, 55 are connected to the rib 70 with a frictional or force fit. Alternatively or in addition, the rods 54, 55 can be joined to the rib 70 by cohesive bonding and/or with a form fit.

In the branch 30 shown in FIG. 7, the jacket 90 completely encloses the branch 30 in the same way already described with reference to FIG. 6.

Figure 8:
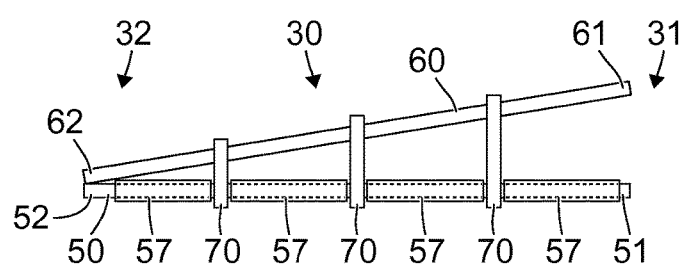
FIG. 8 shows a schematic view of a branch of a further medical gripping tool.

FIG. 8 shows a schematic view of a branch 30 of a further medical gripping tool which, in respect of some features and properties, is similar to the medical gripping tools described above with reference to FIGS. 1 to 5. The plane of the drawing in FIG. 8 corresponds to the planes of the drawings in FIGS. 1 to 5. In contrast to what is shown in FIGS. 2 to 5, however, FIG. 8 does not show a second branch, nor a connection of the first branch 30 to a main body or to a coupling mechanism. Both the proximal end 51 of the first flexurally elastic spar 50 and also the proximal end 61 of the second flexurally elastic spar 60 can each be connected to a main body 26 or to a coupling mechanism 80 (cf. FIGS. 2 to 5) via a hinge (or several hinges) or directly without a hinge.

In contrast to the medical gripping tools described above with reference to FIGS. 1 to 6, and similarly to what is shown in FIG. 7, the first flexurally elastic spar 50 is arranged in recesses in the ribs 70. Similarly to what is shown in FIG. 7, the spar 50 comprises, for example, two or more parallel or substantially parallel flexurally elastic rods.

In contrast to what is shown in FIG. 7, the ribs 70 in the example shown in FIG. 8 are not connected directly and rigidly to the first flexurally elastic spar 50 but are themselves displaceable parallel to the first flexurally elastic spar 50. In order to prevent a displacement of the ribs 70 relative to the first flexurally elastic spar 50, spacer sleeves 57 are provided between the ribs 70 and also between the ribs 70 and the proximal and distal ends 51, 52 of the first flexurally elastic spar 50. The spacer sleeves 57 enclose the flexurally elastic spar 50 or the constituent parts thereof (for example flexurally elastic rods) in particular in a tubular configuration. In order to maintain the flexural elasticity of the first flexurally elastic spar 50, the spacer sleeves 57 are likewise flexurally elastic.

For production, the spacer sleeves 57 and the ribs 70 can be engaged alternately onto the spar 50. The in any case necessary connection of the distal ends 52, 62 of the flexurally elastic spars 50, 60 to each other, and of the proximal ends 51, 61 of the flexurally elastic spars 50, 60 to hinges, to a main body 26 or to a coupling mechanism 80 (cf. FIGS. 2 to 5), means that the spacer sleeves 57 and the ribs 70 are held on both sides and can no longer be moved along the first flexurally elastic spar 50.

REFERENCE SIGNS 10 medical instrument
11 proximal end of the medical instrument 10
12 distal end of the medical instrument 10
13 stationary grip part at the proximal end of the medical instrument 10
14 movable (in particular pivotable) grip part at the proximal end 11 of the medical instrument 10
16 shank of the medical instrument 10
19 object that can be gripped by means of the medical instrument 10
20 medical gripping tool
21 proximal end of the medical gripping tool 20
22 distal end of the medical gripping tool 20
23 hinge between the first branch 30 and the main body 26 of the medical gripping tool 20
24 hinge between the second branch 40 and the main body 26 of the medical gripping tool 20
26 main body
30 first branch of the medical gripping tool 20
31 proximal end of the first branch 30
32 distal end of the first branch 30
39 gripping surface of the first branch 30
40 second branch of the medical gripping tool 20
41 proximal end of the second branch 40
42 distal end of the second branch 40
50 first flexurally elastic spar of the first branch 30
51 proximal end of the first flexurally elastic spar 50
52 distal end of the first flexurally elastic spar 50
54 first flexurally elastic rod of the first spar 50
55 second flexurally elastic rod of the first spar 50
57 spacer sleeve on the first flexurally elastic spar 50
58 fluting on the first flexurally elastic spar 50
60 second flexurally elastic spar of the first branch 30
61 proximal end of the second flexurally elastic spar 60
62 distal end of the second flexurally elastic spar 60
70 rib between the first flexurally elastic spar 50 and the second flexurally elastic spar 60
76 recess in the rib 50 for the second flexurally elastic spar 60
80 coupling mechanism
83 hinge between coupling mechanism 80 and first branch 30
84 hinge between coupling mechanism 80 and second branch 40
90 encapsulating jacket of the flexurally elastic spars 50, 60 and of the rib 70

The invention claimed is:

1. A medical gripping tool with a plurality of branches, wherein one branch comprises:

a first flexurally elastic spar;

a second flexurally elastic spar having a distal end that is connected to a distal end of the first flexurally elastic spar;

a rib, which is spaced apart from proximal ends of the first and second flexurally elastic spars and from the distal ends of the first and second flexurally elastic spars; and a linear guide coupling the second flexurally elastic spar to the rib, in such a way that a linear movement of the second flexurally elastic spar relative to the rib is possible.

2. The medical gripping tool according to claim 1, wherein the rib and the first flexurally elastic spar are connected rigidly to each other.

3. The medical gripping tool according to claim 1, wherein the linear guide comprises a recess in the rib, the second flexurally elastic spar being guided displaceably in the recess in a longitudinal direction of the second flexurally elastic spar.

4. The medical gripping tool according to claim 1, wherein the linear guide comprises an eyelet in which the second flexurally elastic spar is guided displaceably in a longitudinal direction of the second flexurally elastic spar.

5. The medical gripping tool according to claim 1, wherein a plurality of ribs are provided, the ribs are spaced apart from the proximal ends of the first and second flexurally elastic spars and from the distal ends of the first and second flexurally elastic spars and from each other, wherein on each of the plurality of ribs a linear guide is provided which permits a movement of the second flexurally elastic spar relative to the ribs.

6. The medical gripping tool according to claim 1, further comprising:

a fluting on the first flexurally elastic spar.

7. The medical gripping tool according to claim 1, wherein the first flexurally elastic spar at least comprises either two flexurally elastic rods or a component having one or more of a strip-shape or a plate-shape.

8. The medical gripping tool according to claim 1, further comprising:

a spacer sleeve on the first flexurally elastic spar, the spacer sleeve defining a distance of the rib from the proximal end of the first flexurally elastic spar or a distance of the rib from the distal end of the first flexurally elastic spar or a distance of the rib from a further rib.

9. The medical gripping tool according to claim 1, wherein the first flexurally elastic spar, the second flexurally elastic spar and the rib are at least partially encapsulated by an elastic material.

10. The medical gripping tool according to claim 1, further comprising:

a hinge between the proximal end of a branch and a main body.

11. The medical gripping tool according to claim 1, further comprising:

a mechanism for moving the proximal end of the first flexurally elastic spar or the proximal end of the second flexurally elastic spar.

12. A medical instrument comprising:

a medical gripping tool having a plurality of branches;

wherein one branch of the plurality of branches comprises
a first flexurally elastic spar;
a second flexurally elastic spar having a distal end that is connected to a distal end of the first flexurally elastic spar;
a rib, which is spaced apart from proximal ends of the first and second flexurally elastic spars and from the distal ends of the first and second flexurally elastic spars; and
a linear guide coupling the second flexurally elastic spar to the rib, in such a way that a linear movement of the second flexurally elastic spar relative to the rib is possible.

13. The medical gripping tool of claim 1, wherein the linear guide is provided on the rib.

14. The medical gripping tool of claim 12, wherein the linear guide is provided on the rib.

* * * * *